United States Patent
Noguchi (10) Patent No.: US 7,863,049 B2
(45) Date of Patent: Jan. 4, 2011

(54) NONINVASIVE BLOOD SUGAR LEVEL MEASURING METHOD

(75) Inventor: Nobuaki Noguchi, Ehime (JP)

(73) Assignee: Panasonic Corporation, Osaka (JP)

( * ) Notice: Subject to any disclaimer, the term of this patent is extended or adjusted under 35 U.S.C. 154(b) by 268 days.

(21) Appl. No.: 11/785,730

(22) Filed: Apr. 19, 2007

(65) Prior Publication Data

US 2008/0261320 A1    Oct. 23, 2008

(51) Int. Cl.
G01N 33/48 (2006.01)
G01N 33/00 (2006.01)

(52) U.S. Cl. .............................. 436/94; 436/93; 436/91; 422/1; 422/3

(58) Field of Classification Search .................. 436/94, 436/93, 91; 422/82.09, 82.05, 68.1, 50
See application file for complete search history.

(56) References Cited

U.S. PATENT DOCUMENTS 4,882,492 A * 11/1989 Schlager ..................... 250/346
6,226,089 B1   5/2001 Hakamata
6,442,410 B1 *  8/2002 Steffes ....................... 600/319

FOREIGN PATENT DOCUMENTS

JP    2000-37355    2/2000
JP    2003-260041   9/2003

OTHER PUBLICATIONS

Khalil, Omar S., Spectroscopic and Clinical Aspects of Noninvasive Glucose Measurements, 1999, Clinical Chemistry, 45:2, 165-177.*

* cited by examiner

Primary Examiner—Walter D Griffin
Assistant Examiner—Christine T Mui
(74) Attorney, Agent, or Firm—Wenderoth, Lind & Ponack, L.L.P.

(57) ABSTRACT

A noninvasive blood sugar level measurement method includes a process of changing a blood sugar level of a biological body, a process of noninvasively measuring biological feature amounts at plural measurement points that are timewise shifted from each other, a process of invasively measuring blood sugar levels of the biological body by the number of times that is lesser than the measurement points of the biological feature amount, a process of obtaining an approximate curve indicating temporal change in the actually measured blood sugar level that is obtained by the invasive measurement, a process of obtaining, using the obtained approximate curve, blood sugar levels (interpolation blood sugar levels) that would be obtained by the invasive measurement at the measurement times when the biological feature amounts are noninvasively measured, and a process of associating the values of the biological feature amounts at the times corresponding to the respective measurement points of the biological feature amounts with the interpolation blood sugar levels at the respective times, thereby forming a correlation table having plural sets of the biological feature amounts and the interpolation blood sugar levels. Therefore, even when the change in the biological feature amount relative to the blood sugar level is not monotonous, it is possible to form a precise correlation table without increasing the number of times of the invasive blood sugar level measurement.

6 Claims, 5 Drawing Sheets

NONINVASIVE BLOOD SUGAR LEVEL MEASURING METHOD

FIELD OF THE INVENTION

The present invention relates to a noninvasive blood sugar level measuring method for noninvasively measuring a blood sugar level, and more particularly, to a method for forming a correlation table between biological characteristic amounts that are prepared for calculating blood sugar levels, and the blood sugar levels.

BACKGROUND OF THE INVENTION

Conventionally, blood that is collected with a syringe is measured by a high-precision blood sugar analyzer in a hospital or a clinic, and blood that is collected by puncturing a finger tip or the like is measured by a portable and simple blood sugar meter at home or outside home, thereby obtaining a blood sugar level. These measuring methods are called invasive systems. Either method causes pain because a human body is punctured, leading to mental and physical drawbacks in performing measurement and management of the blood sugar level. Further, it is necessary to consider risks of infection diseases as well as disposal of wastes on which blood is attached.

So, blood sugar level measurement methods using various kinds of noninvasive techniques have been proposed. The noninvasive method measures a blood sugar level in a contact or noncontact manner, without hurting a human body, with no pain. As for measurement means, there are proposed electromagnetic wave, acoustic wave, and electrical characteristics, as well as optical rotation or glucose, and absorbance or reflectivity of infrared light or visible light. As for measurement sites, there are proposed skin surfaces of such as arm, finger, and ear, eyeball, nail, sputum, and the like.

In these measurement methods, a blood sugar level in blood vessels is not directly measured, but a biological feature amount relating to a change in the blood sugar level is measured, and it is general to prepare a correlation table between biological feature amounts and blood sugar levels. Since the change in the biological feature amount with respect to the change in the blood sugar level varies among individuals, it is necessary to prepare correlation tables for the respective individuals for accurate measurement.

For example, Japanese Published Patent Application No. 2003-260041 (Patent Document 1) discloses a noninvasive type handy blood sugar level meter, wherein transmittance of light through ear lobule is measured as a biological feature amount, and blood that is collected at the same timing as the measurement timing is analyzed by an accurate analyzer to measure a blood sugar level, and then a correlation table showing correlation between the blood sugar level and the biological feature amount is prepared.

On the other hand, Japanese Published Patent Application No. 2000-37355 (FIG. 6) proposes a glucose concentration measurement method and apparatus adopting an eyeball as a measurement site, wherein a change of refractive index in aqueous humor is measured as a biological feature amount, and correlation between the refractive index and a glucose concentration in the aqueous humor is utilized. In such method and apparatus, when the correlation between the blood sugar level and the biological feature amount can be approximated by a primary straight line, a correlation table that is obtained by several points including low blood sugar levels and high blood sugar levels is prepared, whereby a blood sugar level can be estimated using the primary straight line if a biological feature amount that is not included in the correlation table is obtained.

Figure 6:
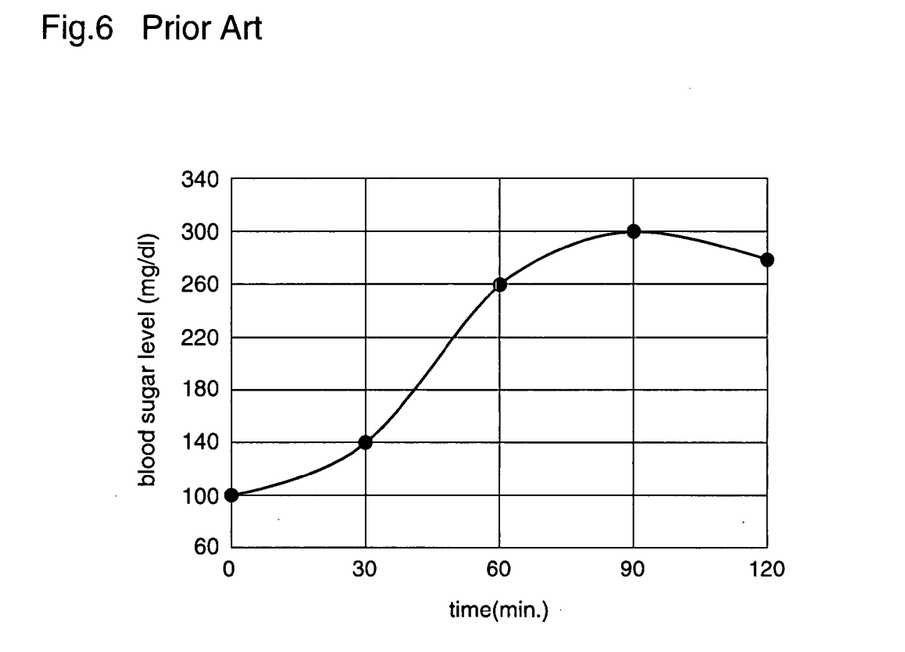
FIG. 6 is a diagram illustrating actually measured blood sugar levels that are obtained by the conventional invasive blood sugar level measurement method, and a time change curve thereof.

FIG. 6 shows an example of a sugar tolerance test by sugar ingestion. In FIG. 6, five circles indicate measurement points that are obtained by performing invasive blood sugar measurement for every 30 minutes. The blood sugar level at time 0 minute is 100 mg/dl, and it increases to 140 mg/dl in 30 minutes, to 260 mg/dl in 60 minutes, to 300 mg/dl in 90 minutes, and then decreases to 280 mg/dl in 120 minutes. With reference to these five points of blood sugar levels, the time change curve of the blood sugar level can be approximated as a solid line shown in FIG. 6.

Figure 7:
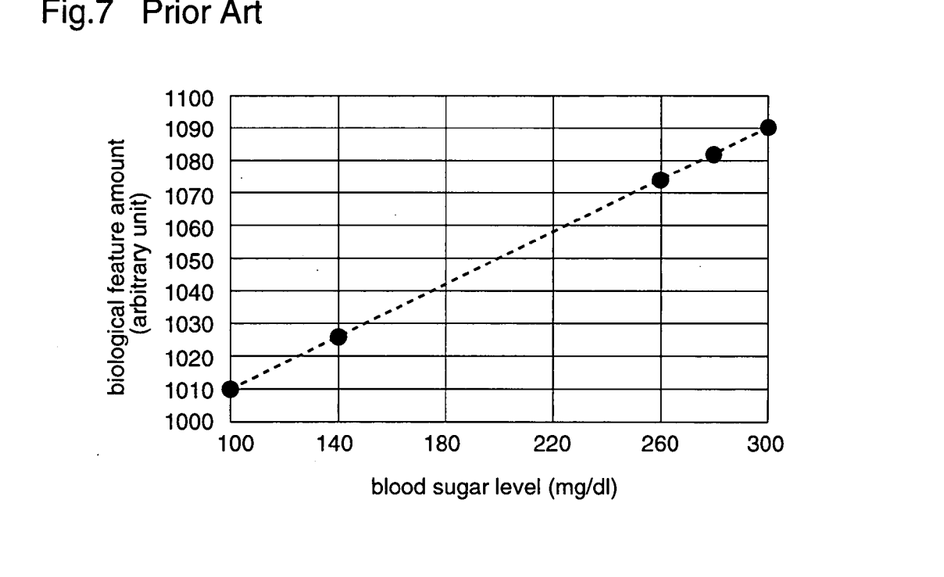
FIG. 7 is a diagram illustrating a conventional relationship between a blood sugar level and a biological feature amount in the case where the relationship is monotonous.

FIG. 7 shows a case where the relation ship between the blood sugar level and the biological feature amount can be approximated by a primary straight line. When the blood sugar level changes from 100 mg/dl to 300 mg/dl, the biological feature amount monotonically increases from 1010 to 1090. In the case where the blood sugar level and the biological feature amount can be approximated by a primary straight line as described above, if a correlation table between the five points of blood sugar levels and the corresponding biological feature amounts is prepared in advance, the blood sugar level can be estimated as 200 mg/dl and 225 mg/dl when the biological feature amount obtained by the noninvasive measurement is 1050 and 1060, respectively.

However, the biological feature amount that is obtained from a transmission amount, or an absorption amount, or a reflection amount of an electromagnetic wave, or an acoustic wave, or an optical wave which are applied to a biological body, or from spatial distribution of the transmission amount, or spatial distribution of the absorption amount, or spatial distribution of the reflection amount is adversely affected by multiple reflection/scattering, or interference. Therefore, usually, the biological feature amount does not change monotonically.

Figure 8:
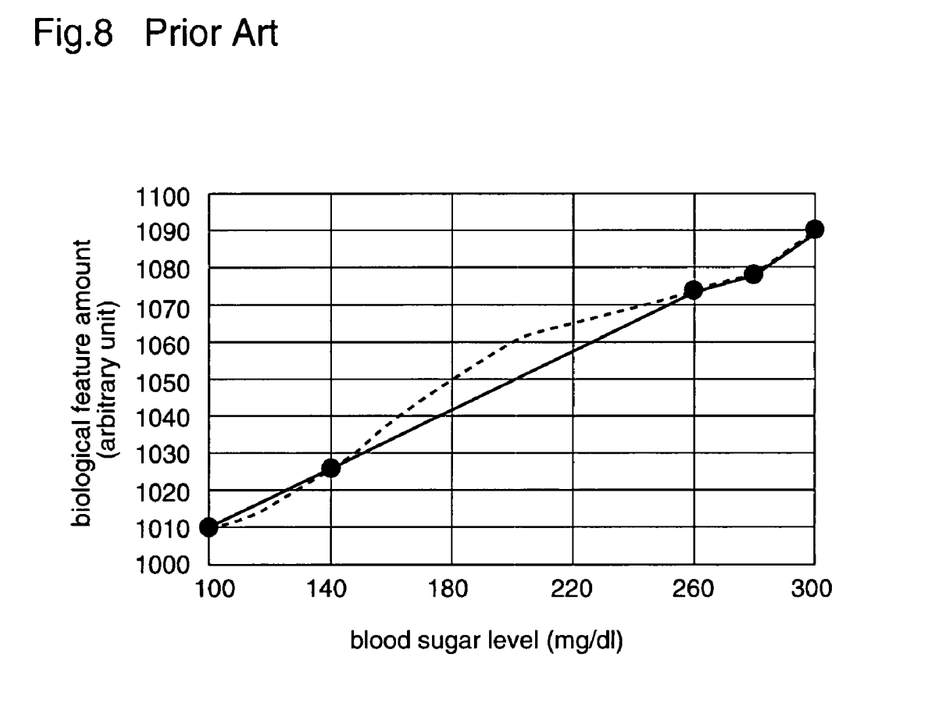
FIG. 8 is a diagram illustrating a conventional relationship between a blood sugar level and a biological feature amount in the case where the relationship is not monotonous.

FIG. 8 shows the case where the relationship between the blood sugar level and the biological feature amount is not a primary straight line. In this case, since only a change in the biological feature amount as shown by a solid line in FIG. 8 can be estimated from the above-mentioned five points, the original change in the biological feature amount that is indicated by a broken line cannot be traced. For example, when the biological feature amount is 1050, the blood sugar level is estimated as 200 mg/dl although the correct blood sugar level is 180 mg/dl.

Of course, it is possible to accurately trace the change in the biological feature amount if plural blood sugar levels are previously obtained by performing a considerable number of invasive blood sugar level measurements. However, this method brings considerable pain on the subject.

In the conventional noninvasive blood sugar level measurement method, when the relationship between the blood sugar level and the biological feature amount is not the simple primary straight line, it is difficult to obtain an accurate correlation table. Further, performing many times of invasive blood sugar level measurements to obtain an accurate correlation table leads to an increase in the pain on the subject.

SUMMARY OF THE INVENTION

The present invention is made to solve the above-mentioned problems and has for its object to provide a noninvasive blood sugar level measurement method which can provide a highly accurate correlation table without increasing the number of times of invasive blood sugar level measurements, and thereby performs highly precise noninvasive measurement of blood sugar level.

Other objects and advantages of the invention will become apparent from the detailed description that follows. The detailed description and specific embodiments described are provided only for illustration since various additions and modifications within the scope of the invention will be apparent to those of skill in the art from the detailed description.

According to a first aspect of the present invention, there is provided a noninvasive blood sugar level measurement method including a process of obtaining a correlation between a blood sugar level of a biological body and a biological feature amount that is noninvasively obtained, and the method comprises a process of changing the blood sugar level of the biological body; a process of noninvasively measuring the biological feature amount at plural measurement points that are timewise shifted from each other; a process of invasively measuring the blood sugar level of the biological body by the number of times that is lesser than the measurement points of the biological feature amount; a process of obtaining an approximate curve indicating temporal change in the actually measured blood sugar level that is obtained by the invasive measurement; a process of obtaining, using the obtained approximate curve, blood sugar levels (hereinafter referred to as interpolation blood sugar levels) that would be obtained by the invasive measurement at the measurement times when the biological feature amounts are noninvasively measured; and a process of associating the values of the biological feature amounts at the times corresponding to the respective measurement points of the biological feature amounts with the interpolation blood sugar levels at the respective times, thereby forming a correlation table having plural sets of the biological feature amounts and the interpolation blood sugar levels.

According to a second aspect of the present invention, in the noninvasive blood sugar level measurement method according to the first aspect, the biological feature amount is a transmission amount, or an absorption amount, or a reflection amount of an electromagnetic wave, or an acoustic wave, or an optical wave that is applied to the biological body, or from spatial distribution of the transmission amount, or spatial distribution of the absorption amount, or spatial distribution of the reflection amount.

According to a third aspect of the present invention, in the noninvasive blood sugar level measurement method according to the first aspect, the process of varying the blood sugar level of the biological body is performed by ingestion of sugar; and when the actually measured blood sugar level turns from increase to decrease, the process of noninvasively measuring the biological feature amount an the process of invasively measuring the blood sugar level of the biological body are terminated.

According to a fourth aspect of the present invention, in the noninvasive blood sugar level measurement method according to the first aspect, the process of varying the blood sugar level of the biological body is performed by administration of insulin; and when the actually measured blood sugar level decreases to a predetermined blood sugar level, the process of noninvasively measuring the biological feature amount and the process of invasively measuring the blood sugar level of the biological body are terminated.

According to a fifth aspect of the present invention, in the noninvasive blood sugar level measurement method according to the first aspect, the time interval for noninvasively measuring the biological feature amount is not shorter than one minute and not longer than five minutes.

According to a sixth aspect of the present invention, in the noninvasive blood sugar level measurement method according to the first aspect, the time interval for invasively measuring the blood sugar level is longer than the time interval for noninvasively measuring the biological feature amount, and is not longer than 30 minutes.

According to a seventh aspect of the present invention, in the noninvasive blood sugar level measurement method according to the first aspect, the process of forming the correlation table includes a process of comparing the biological feature amounts at the adjacent previous and next interpolation blood sugar levels within a range where the biological feature amount relative to the interpolation blood sugar level changes monotonically, and selecting an interpolation blood sugar level at which a difference of the biological feature amounts is minimum; and a process of deleting the selected interpolation blood sugar level from the correlation table.

According to an eighth aspect of the present invention, the noninvasive blood sugar level measurement method according to any of the first to seventh aspects further includes a process of noninvasively measuring a current biological feature amount; and a process of obtaining a current blood sugar level from the measured current biological feature amount with reference to the correlation table that is formed in the correlation table formation process.

EFFECTS OF THE INVENTION

According to the noninvasive blood sugar level measurement method of the present invention, even when the change in the biological feature amount relative to the blood sugar level is not monotonous, interpolation blood sugar levels are obtained from an approximate curve indicating temporal change in the actually measured blood sugar level without increasing the number of times of invasive blood sugar level measurement, and an accurate correlation table between the interpolation blood sugar levels and the biological feature amounts is formed. Therefore, an accurate current blood sugar level can be obtained from a current biological feature amount that is noninvasively obtained, with reference to the correlation table.

DETAILED DESCRIPTION OF THE PREFERRED EMBODIMENTS

Hereinafter, an embodiment of a noninvasive blood sugar level measurement method according to the present invention will be described with reference to the drawings.

Embodiment 1

Figure 1:
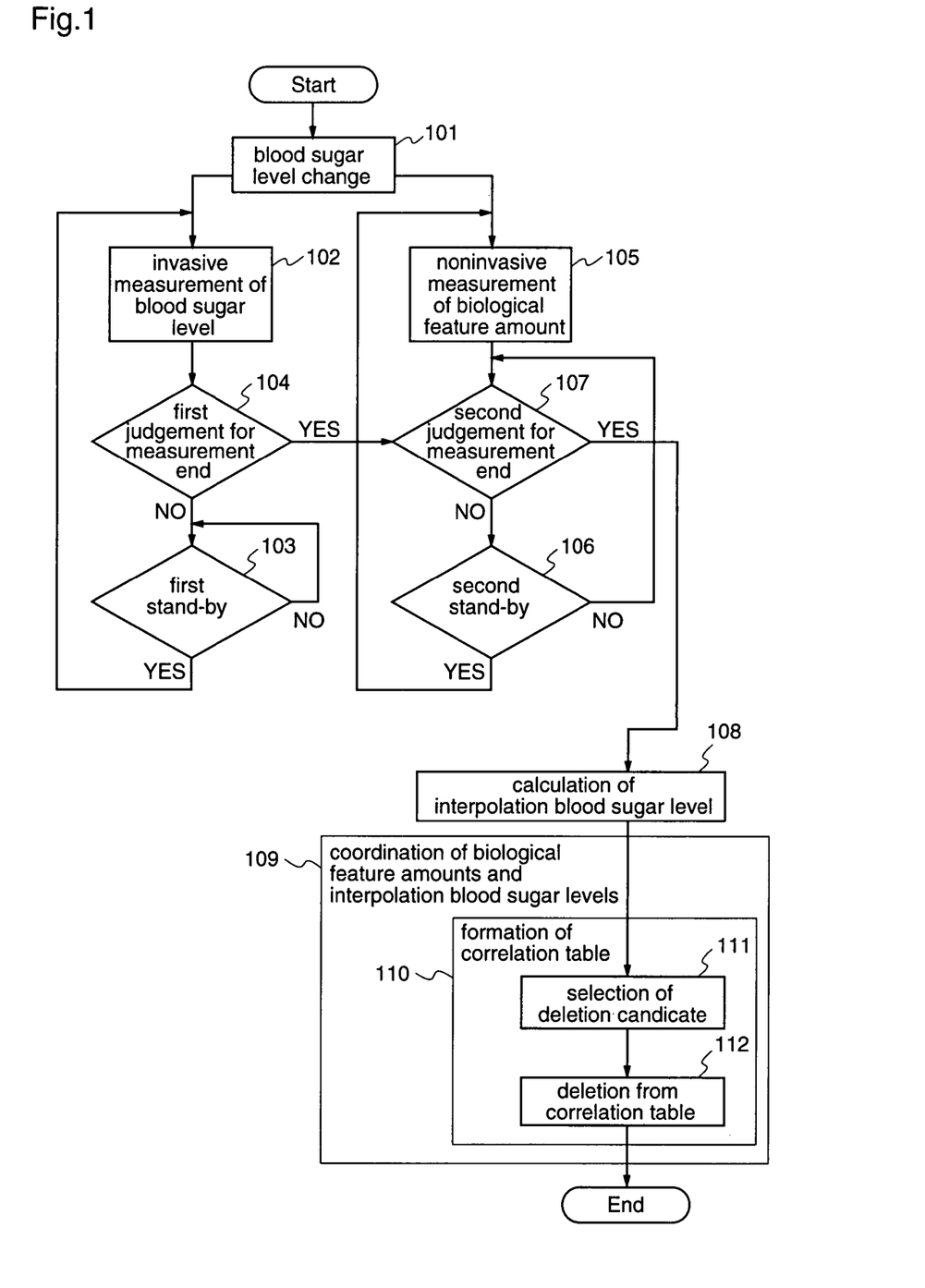
FIG. 1 is a flowchart for explaining a noninvasive blood sugar level measurement method according to a first embodiment of the present invention.

FIG. 1 is a diagram illustrating a noninvasive blood sugar level measurement method according to a first embodiment of the present invention.

With reference to FIG. 1, the noninvasive blood sugar level measurement method according to the first embodiment comprises a process 101 of varying a blood sugar level of a biological body, a process 102 of invasively measuring a blood sugar level of the biological body by the number of times that is less than the number of measurement points of biological feature amounts which will be described later, a first measurement termination judgment process 104 of judging whether the blood sugar level measuring process 102 should be repeated or not, a first stand-by process 103 of waiting until the blood sugar level measuring process 102 is again performed, a process 105 of noninvasively measuring a biological feature amount at plural measurement points that are timewise shifted from each other, a second measurement termination judgment process 107 of judging whether the biological feature amount measuring process 105 should be repeated or not, a second stand-by process 106 of waiting until the biological feature amount measuring process 105 is again performed, a process 108 of obtaining blood sugar levels (hereinafter referred to as interpolation blood sugar levels) which would be obtained by the invasive measurement at the times when the biological feature amounts are noninvasively obtained, and a process 109 of associating the values of the biological feature amounts a the points corresponding to the respective measurement times thereof, with the interpolation blood sugar levels at the times. The process 109 includes a correlation table formation process 110 of forming a correlation table having plural sets of the biological feature amounts and the interpolation blood sugar levels, and the correlation table formation process 110 includes a deletion candidate selection process 111 of comparing the biological feature amounts at the adjacent previous and next interpolation blood sugar levels within a range where the biological feature amount relative to the interpolation blood sugar level changes monotonically, and selecting interpolation blood sugar levels at which a difference between the biological feature amounts becomes minimum, and a correlation table reduction process 112 of deleting the selected interpolation blood sugar levels from the correlation table.

Hereinafter, the respective processes of the noninvasive blood sugar level measurement method according to the first embodiment will be specifically described with reference to a flowchart shown in FIG. 1.

Initially, in the blood sugar level varying process 101, the blood sugar level of the biological body is varied. To be specific, the subject to be tested takes sugar to make a blood sugar level change with in a range in which the blood sugar level of each biological body usually varies. At this time, it is desired that the blood sugar level reaches the lowest level by fasting or taking enough time after meal.

Next, the invasive blood sugar level measurement process 102 and the noninvasive biological feature amount measurement process 105 are started.

In the invasive blood sugar level measurement process 102, blood is collected from the biological body to measure a blood sugar level, and this process causes suffering of the subject. This measurement process may be carried out with a highly precise stationary device using blood plasma that is centrifugal-separated after the blood collection, or a portable blood sugar level meter using blood that is collected from a finger tip by a puncture needle.

Further, since the precision of the blood sugar level that is obtained in the invasive blood sugar level measurement process 102 (hereinafter referred to as an actually measured blood sugar level) is important to accurately perform noninvasive biological feature amount measurement in the noninvasive biological feature amount measurement process 105, it is preferable to obtain an actually measured blood sugar level using a highly precise stationary device.

Although the invasive blood sugar level measurement process 102 is repeatedly performed, the operation stands by at the first stand-by process 103 until the next invasive blood sugar level measurement process 102 is carried out.

Now, a time interval for repeating the invasive blood sugar level measurement process 102 is set so that the actually measured blood sugar levels obtained in the invasive blood sugar level measurement process 102 are those obtained by the minimum number of measurements for obtaining a time change curve of the blood sugar level.

While the blood sugar level change width of the time change curve of the blood sugar level and the time required until the blood sugar level reaches the maximum level differ depending on whether the subject is a diabetic patient or a healthy subject, the first time interval to be set in the invasive blood sugar level measurement process 102 is desired to be 30 minutes or less in order to obtain at least four points of actually measured blood sugar levels.

The actually measured blood sugar levels obtained in the invasive blood sugar level measurement process 102 are recorded together with the measurement times.

Further, the first measurement termination judgment process 104 judges whether the measurement in the invasive blood sugar level measurement process 102 is terminated or not, and terminates the invasive blood sugar level measurement process 102. Termination of the invasive blood sugar level measurement process 102 can be judged by that a predetermined period of time has passed or that a predetermined number of measurements have been performed. Alternatively, the termination of the invasive blood sugar level measurement process 102 may be judged at the timing when the actually measured blood sugar level reaches the maximum level and then turns to decrement.

On the other hand, also the noninvasive biological feature amount measurement process 105 for noninvasively measuring biological feature amounts is repeatedly carried out, and the measured biological feature amounts are recorded together with the measurement times. The biological feature amounts can be obtained from a transmission amount, or an absorption amount, or a reflection amount of an electromagnetic wave, or an acoustic wave, or an optical wave, or from spatial distribution of the transmission amount, or spatial distribution of the absorption amount, or spatial distribution of the reflection amount.

When the change in the biological feature amount due to the change in the blood sugar level is not monotonous, the noninvasive biological feature amount measurement process 105 may be executed plural times to trace the change in the biological feature amount. Therefore, the stand-by time of the second stand-by process 106 is made shorter than the stand-by time of the first stand-by process 103. Especially when the change in the biological feature amount is larger than the change in the blood sugar level, an interval not shorter than one minute and not longer than five minutes is required.

Even when the noninvasive biological feature measurement process 105 is repeated plural times at the above-mentioned time interval, since the noninvasive measurement does not injure the biological body of the subject an causes no pain on the subject in contrast to the invasive blood sugar level measurement, burden on the subject is reduced.

The second measurement termination judgment process 107 judges whether the measurement in the noninvasive biological feature amount measurement process 105 is terminated or not, and terminates the noninvasive biological feature amount measurement process 105. Termination of the noninvasive biological feature amount measurement process 105 can be judged by that a predetermined period of time has passed or that a predetermined number of measurements have been performed, similarly as in the first measurement termination judgment process 104.

Further, it is possible to judge termination of the noninvasive biological feature amount measurement process 105 on receipt of the result that the first measurement termination judgment process 104 has judged the termination.

FIG. 1 shows the latter case. Particularly, when termination of the invasive blood sugar level measurement process 102 is judged, repetition of the noninvasive biological feature amount measurement process 105 is terminated.

Further, although it is not shown in the figure, if the second measurement termination judgment process 107 is executed prior to the waiting (stand-by) loop of the second stand-by process 106, it is possible to terminate the second measurement after executing the noninvasive biological feature amount measurement process 105 only one more time, after the first measurement termination judgment process 104 judges termination.

Next, association of the blood sugar level of the biological body with the biological feature amount is carried out as follows.

That is, in the interpolation blood sugar level calculation process 108, a blood sugar level at the time when the noninvasive biological feature amount measurement process 105 is carried out is calculated on the basis of the actually measured blood sugar level obtained in the invasive blood sugar level measurement process 102 and the measurement time thereof. To be specific, an approximate curve of the time change of the blood sugar level is obtained from the actually measured blood sugar levels that are obtained in the invasive blood sugar level measurement process 102, and interpolation blood sugar levels at the respective times when the biological feature amounts are measured in the noninvasive biological feature amount measurement process 105 are obtained.

In the process 109 for associating the biological feature amounts with the interpolation blood sugar levels, the biological feature amounts obtained in the noninvasive biological feature amount measurement process 105 are associated with the interpolation blood sugar levels at the corresponding times. Further, the correlation table formation process 110 that is included in the association process 109 forms a correlation table comprising plural sets of the biological feature amounts and the interpolation blood sugar levels. This correlation table is referred to in an estimation blood sugar level calculation process 502 to be described later.

By the way, as another method of the blood sugar level change process 101, administration of insulin may be performed. In this case, insulin is administered with the blood sugar level being high, and the first measurement termination judgment process 104 judges termination when the blood sugar level reaches about 50 mg/dl that is called hypoglycemia.

However, since the hypoglycemic state causes various symptoms in the biological body, it is necessary to recover the blood sugar level to a safe level by taking sugar.

Figure 2:
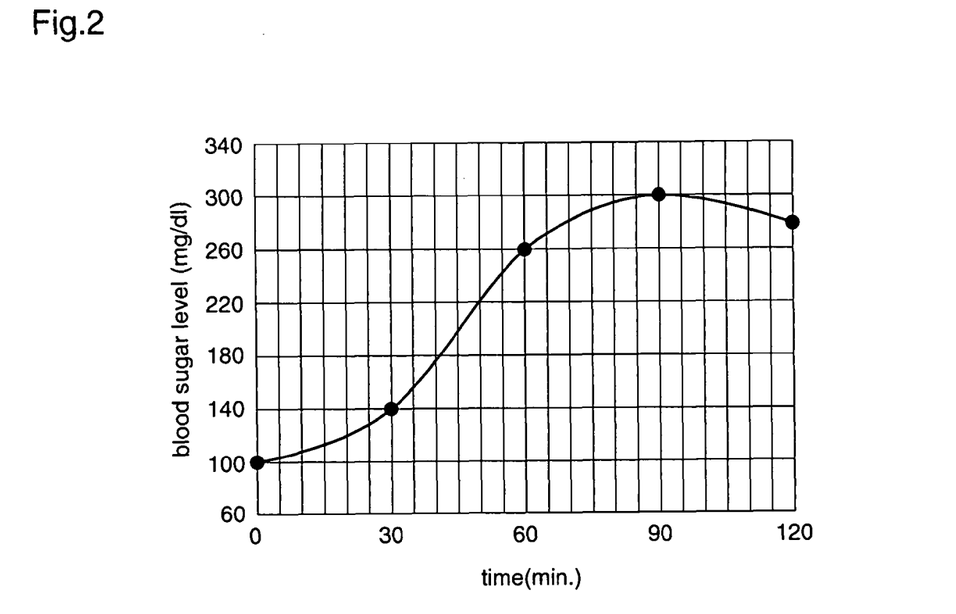
FIG. 2 is a diagram illustrating actually measured blood sugar levels that are obtained by invasive blood sugar level measurement and a time change curve thereof according to the first embodiment of the present invention.

FIG. 2 shows an example of measurement of actually measured blood sugar levels in the noninvasive blood sugar level measurement method according to the first embodiment.

The invasive blood sugar level measurement process 102 is performed every 30 minutes. Since the blood sugar level at the fifth measurement is lower than that at the fourth measurement, the invasive blood sugar level measurement process 102 is terminated. In FIG. 2, five black dots indicate the results of the actually measured blood sugar levels. The blood sugar level at time 0 minute is 100 mg/dl, and it increases to 140 mg/dl in 30 minutes, to 260 mg/dl in 60 minutes, and to 300 mg/dl in 90 minutes, and decreases to 280 mg/dl in 120 minutes.

From these actually measured blood sugar levels, the time change curve of the blood sugar level can be approximated as shown by the solid line in FIG. 2.

On the other hand, the noninvasive biological feature amount measurement is carried out at intervals of 5 minutes from time 0 minute, thereby calculating the biological feature amounts at the respective times. The interpolation blood sugar levels at the respective times can be obtained from the approximate curve shown in FIG. 2.

TABLE 1

| time | interpolation blood sugar level | biological feature amount |
|---|---|---|
| 0 | 100 | 1010 |
| 5 | 106 | 1011 |
| 10 | 111 | 1012 |
| 15 | 116 | 1014 |
| 20 | 121 | 1016 |
| 25 | 129 | 1020 |
| 30 | 140 | 1026 |
| 35 | 155 | 1034 |
| 40 | 176 | 1048 |
| 45 | 200 | 1060 |
| 50 | 222 | 1065 |
| 55 | 243 | 1070 |
| 60 | 260 | 1074 |
| 65 | 272 | 1075 |
| 70 | 281 | 1078 |
| 75 | 289 | 1082 |
| 80 | 294 | 1085 |
| 85 | 298 | 1087 |
| 90 | 300 | 1090 |

Table 1 is an example of a correlation table, in which the interpolation blood sugar levels obtained from 0 minute to 90 minutes at which the blood sugar level becomes maximum are associated with the biological feature amounts.

Figure 3:
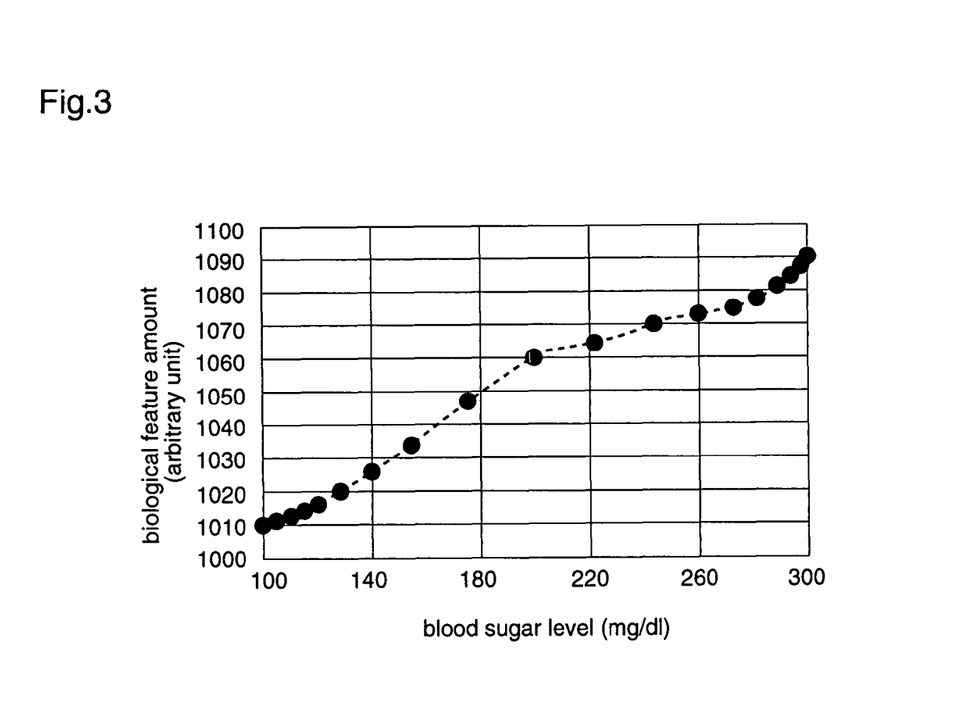
FIG. 3 is a diagram illustrating a relationship between an interpolation blood sugar level and a biological feature amount according to the first embodiment of the present invention.

Further, FIG. 3 illustrates a relationship between the interpolation blood sugar level and the biological feature amount. In FIG. 3, a dotted line is a curve indicating the change in the biological feature amount relative to the blood sugar level. When the black dots obtained from the correlation table are connected, it is found that the broken line indicating the change in the biological feature amount relative to the blood sugar level is traced.

While all the results of the noninvasive biological feature amount measurement be included in the correlation table, if it is required to reduce the number of the values included in the correlation table, some of the interpolation blood sugar levels which concentrate in a region where the change in the biological feature amount is monotonous can be deleted.

In the deletion candidate selection process 111 included in the correlation table formation process 110, the biological feature amounts corresponding to the adjacent previous and next interpolation blood sugar levels are compared within a range where the biological feature amount relative to the interpolation blood sugar level changes monotonically, and an interpolation blood sugar level at which a difference between the biological feature amounts becomes minimum is selected. To be specific, when continuous three points of biological feature amounts are in monotonic increase or decrease and the change in the continuous three points of biological feature amounts is minimum, the center point is selected as a deletion candidate.

In the correlation table deletion process 112 included in the correction table formation process 110, the deletion candidate that is selected in the deletion candidate selection process 111 is deleted from the current correlation table.

TABLE 2

| time | interpolation blood sugar level | biological feature amount |
| --- | --- | --- |
| 0 | 100 | 1010 |
| 20 | 121 | 1016 |
| 30 | 140 | 1026 |
| 35 | 155 | 1034 |
| 40 | 176 | 1048 |
| 45 | 200 | 1060 |
| 50 | 222 | 1065 |
| 55 | 243 | 1070 |
| 60 | 260 | 1074 |
| 70 | 281 | 1078 |
| 90 | 300 | 1090 |

Figure 4:
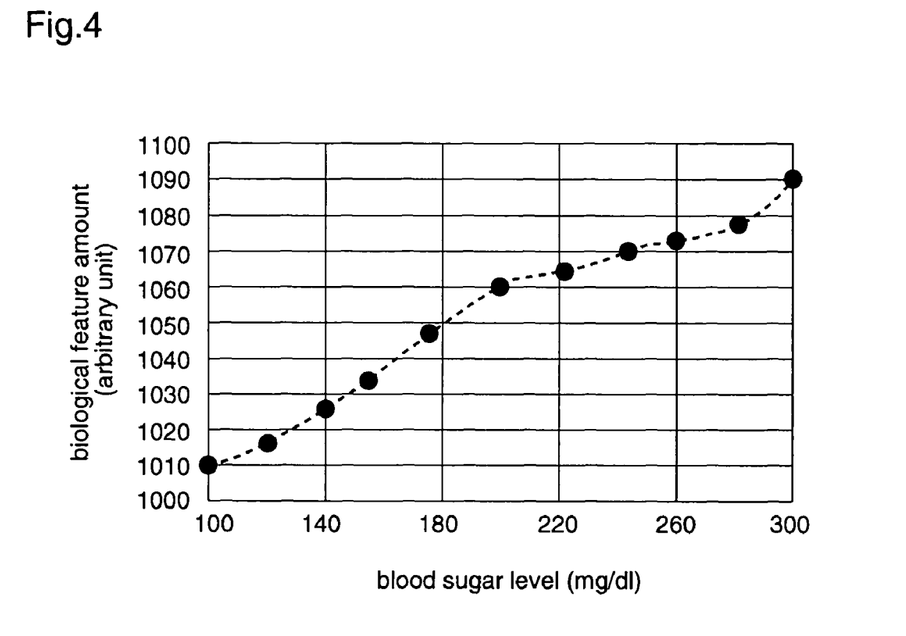
FIG. 4 is a diagram illustrating a relationship between the interpolation blood sugar level after deletion and the biological feature amount according to the first embodiment of the present invention.

Table 2 is an example of a correlation table from which deletion candidates are deleted, and FIG. 4 shows a relationship between the interpolation blood sugar level and the biological feature amount after the deletion. In FIG. 4, when the black dots obtained from the correlation table, which are reduced to eleven, are connected, it is found that the broken line indicating the change in the biological feature amount relative to the blood sugar level can be traced in the same manner as shown in FIG. 3.

Accordingly, by performing the deletion candidate selection process 111 and the correlation table deletion process 112, the delectable interpolation blood sugar levels are deleted from the correlation table in the range where the change in the biological feature amount is monotonous, while the interpolation blood sugar levels are left in the correlation table in the region where the change in the biological feature amount is irregular, thereby obtaining the correlation table having less sets of the biological feature amounts and the interpolation blood sugar levels.

Figure 5:
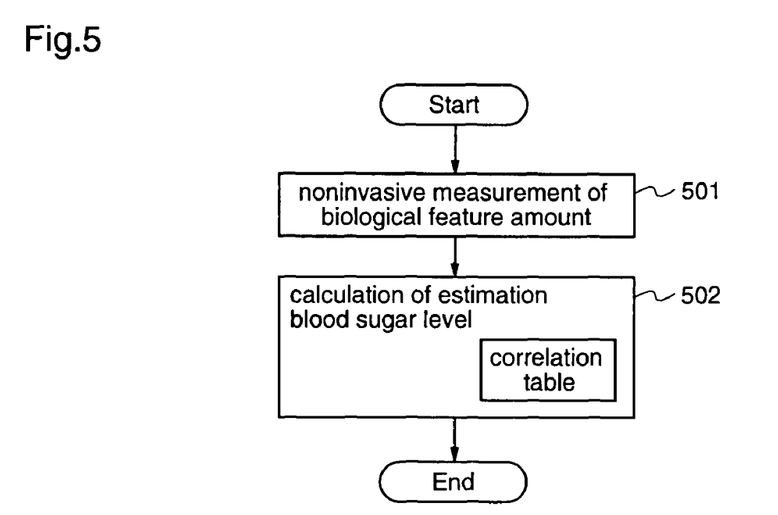
FIG. 5 is a flowchart of a noninvasive blood sugar level measurement method for obtaining a current blood sugar level according to the first embodiment of the present invention.

FIG. 5 shows a flowchart for explaining a method of obtaining, particularly, a current blood sugar level, in the noninvasive blood sugar level measurement method according to the first embodiment.

The method of obtaining the current blood sugar level includes a noninvasive biological feature amount measurement process 501 and an estimation blood sugar level calculation process 502. Hereinafter, the details of the respective processes and the procedure will be described.

Initially, when the current blood sugar level is required, the biological feature amount is measured noninvasively in the noninvasive biological feature amount measurement process 501. Thereafter, in the estimation blood sugar level calculation process 502, the current blood sugar level can be obtained with reference to the correlation table that is prepared in advance.

For example, assuming that the correlation table 2 is prepared in advance, when the biological feature amount obtained in the noninvasive measurement process 501 is 1050, since it corresponds to a value between the biological feature amounts 1048 and 1060 (the ratio of 2:10) on the correlation table, the estimation blood sugar level is calculated as 180 mg/dl on the basis of the corresponding interpolation blood sugar levels 176 mg/dl and 200 mg/dl, respectively.

The above-mentioned change in the biological feature amount relative to the blood sugar level is merely an example, and it varies differently depending on the biological feature amount detection means and the individual differences of the subjects.

According to the first embodiment of the present invention, the noninvasive blood sugar level measurement method including the process of obtaining a correlation between a blood sugar level of a biological body and a biological feature amount that is noninvasively obtained, further includes a process of changing the blood sugar level of the biological body, a process of noninvasively measuring the biological feature amount at plural measurement points that are timewise shifted from each other, a process of invasively measuring the blood sugar level of the biological body by the number of times that is lesser than the measurement points of the biological feature amount, a process of obtaining an approximate curve indicating the temporal change in the actually measured blood sugar level that is obtained by the invasive measurement, a process of obtaining, using the obtained approximate curve, blood sugar levels that would be obtained by the invasive measurement at the measurement times when the biological feature amounts are noninvasively measured, and a process of associating the values of the biological feature amounts at the times corresponding to the respective measurement points of the biological feature amounts with the interpolation blood sugar levels at the respective times, thereby forming a correlation table having plural sets of the biological feature amounts and the interpolation blood sugar levels. Therefore, even when the change in the biological feature amount relative to the blood sugar level is not monotonous, a highly precise correlation table between the biological feature amount and the interpolation blood sugar level can be obtained without increasing the number of times of the invasive blood sugar level measurement, and thereby an accurate current blood sugar level can be obtained from the current biological feature amount that is noninvasively obtained, with reference to the correlation table.

APPLICABILITY IN INDUSTRY

A noninvasive blood sugar level measurement method according to the present invention can provide a highly precise correlation table without increasing the number of times of invasive blood sugar level measurements even when the change in the biological feature amount relative to the blood sugar level is not monotonous, and therefore, it is useful in noninvasive blood sugar level measurement for which a correlation table must be prepared in advance.

What is claimed is:

1. A noninvasive blood sugar level measurement method including obtaining a correlation for respective individuals between a blood sugar level of a biological body and a biological feature amount that is obtained by performing noninvasive measurement, said process of obtaining the correlation for the respective individuals comprising:

varying the blood sugar level of the biological body;

measuring the biological feature amount by temporally performing plural times of noninvasive measurements at first time intervals within a predetermined period, after varying the blood sugar level of the biological body;

measuring the blood sugar level of the biological body by temporally performing invasive blood sugar measurements at second time intervals which are not synchronized with said first time intervals and are longer than said first time intervals within the predetermined period, the number of times of which is less than that of the noninvasive measurements, after varying the blood sugar level of the biological body;

obtaining an approximate curve indicating temporal change in the blood sugar level in the predetermined period from the blood sugar level of the biological body which is obtained by the invasive blood sugar measurement;

obtaining, using the approximate curve, blood sugar levels (hereinafter referred to as interpolation blood sugar levels) which are supposed to be obtained by the invasive blood sugar measurements corresponding to the respective times at which the noninvasive measurements were performed;

associating the biological feature amounts which are obtained at the respective times of the noninvasive measurements with the obtained interpolation blood sugar levels, thereby forming a correlation table having plural sets of the biological feature amounts and the interpolation blood sugar levels; and eliminating the interpolation blood sugar level values in a range in which the biological feature amounts vary monotonously, with the remaining interpolation blood sugar level values in a range in which the biological feature amounts vary irregularly, measuring current biological feature amounts by performing noninvasive measurement, extracting two biological feature amounts which are between the current biological feature amounts from the correlation table in which the interpolation blood sugar levels are eliminated, and calculating the interpolation blood sugar levels from the ratio between the current biological feature amounts and the two biological feature amounts to obtain the current estimated blood sugar level.

2. A noninvasive blood sugar level measurement method as defined in claim 1 wherein said biological feature amount is a transmission amount, or an absorption amount, or a reflection amount of an electromagnetic wave, or an acoustic wave, or an optical wave that is applied to the biological body, or from spatial distribution of the transmission amount, or spatial distribution of the absorption amount, or spatial distribution of the reflection amount.

3. A noninvasive blood sugar level measurement method as defined in claim 1 wherein varying the blood sugar level of the biological body is performed by ingestion of sugar; and when the blood sugar level which is obtained by the invasive blood sugar measurement turns from increase to decrease, the predetermined periods in the process of measuring the biological feature amount by the noninvasive measurement and in the process of measuring the blood sugar level of the biological body using the invasive blood sugar measurement are terminated.

4. A noninvasive blood sugar level measurement method as defined in claim 1 wherein varying the blood sugar level of the biological body is performed by administration of insulin; and when the blood sugar level obtained by the invasive blood sugar measurement decreases to a predetermined blood sugar level, the predetermined periods in the process of measuring the biological feature amount by the noninvasive measurement and in the process of measuring the blood sugar level of the biological body using the invasive blood sugar measurement are terminated.

5. A noninvasive blood sugar level measurement method as defined in claim 1 wherein said first time intervals are not longer than five minutes.

6. A noninvasive blood sugar level measurement method as defined in claim 1 wherein said second time intervals are not longer than 30 minutes.

* * * * *